(12) United States Patent
Blomberg

(10) Patent No.: US 8,673,328 B2
(45) Date of Patent: *Mar. 18, 2014

(54) TOPICAL SKIN COMPOSITION COMPRISING SHEA BUTTER, JOJOBA OIL, PETROLEUM JELLY, STEARIC ACID, MAGNESIUM SULFATE, ZINC OXIDE, GLYCERIN, AND WATER

(76) Inventor: Agnes Mwangi Blomberg, Sturbridge, MA (US)

( * ) Notice: Subject to any disclaimer, the term of this patent is extended or adjusted under 35 U.S.C. 154(b) by 54 days.

This patent is subject to a terminal disclaimer.

(21) Appl. No.: 12/758,006

(22) Filed: Apr. 11, 2010

(65) Prior Publication Data

US 2011/0250293 A1  Oct. 13, 2011

(51) Int. Cl.

| A61K 8/00 | (2006.01) |
| A61K 8/02 | (2006.01) |
| A61K 31/01 | (2006.01) |
| A61K 31/045 | (2006.01) |
| A61K 36/00 | (2006.01) |
| A61K 8/18 | (2006.01) |
| A61K 8/27 | (2006.01) |
| A61K 8/31 | (2006.01) |
| A61K 8/36 | (2006.01) |
| A61K 8/92 | (2006.01) |
| A61K 8/97 | (2006.01) |
| A61K 47/06 | (2006.01) |
| A61K 47/12 | (2006.01) |
| A61K 47/44 | (2006.01) |

(52) U.S. Cl.
CPC ... *A61K 8/18* (2013.01); *A61K 8/27* (2013.01); *A61K 8/31* (2013.01); *A61K 8/36* (2013.01); *A61K 8/92* (2013.01); *A61K 8/97* (2013.01); *A61K 2201/20* (2013.01); *A61K 47/06* (2013.01); *A61K 47/12* (2013.01); *A61K 47/44* (2013.01)
USPC ........... 424/401; 424/59; 424/63; 424/64; 424/642; 424/725; 514/738; 514/762

(58) Field of Classification Search
None
See application file for complete search history.

(56) References Cited

U.S. PATENT DOCUMENTS

2008/0152722 A1 * 6/2008 Norburn ................ 424/539

* cited by examiner

*Primary Examiner* — Kevin S Orwig

(57) ABSTRACT

The present invention relates to compositions and methods for the treatment of topical skin conditions, comprising of cocoa butter, petroleum jelly, jojoba oil, dihydrogen oxide, Stearic acid, Anhydrous Magnesium Sulphate, Zinc Oxide, Glycerin and a suitable amount of a pharmaceutically acceptable shea butter.

10 Claims, No Drawings

TOPICAL SKIN COMPOSITION COMPRISING SHEA BUTTER, JOJOBA OIL, PETROLEUM JELLY, STEARIC ACID, MAGNESIUM SULFATE, ZINC OXIDE, GLYCERIN, AND WATER

REFERENCES CITED

| U.S. Patent Documents | | |
|---|---|---|
| 7,429,386 | September, 2008 | First |
| 6,596, 287 | July, 2003 | Deckers, et al. |
| EP1750660 | March, 1930 | McClung |
| 5,134,163 | July, 1992 | Kligman |
| 4,603,146 | July, 1986 | Kligman |
| 4,165,385 | August, 1979 | Lefebvre |
| 4,454,118 | June, 1984 | Johnson |
| 5,503,825 | April, 1996 | Lane |

FIELD OF THE INVENTION

The present invention relates to a composition comprising of Shea butter, Cocoa Butter (*theobroma cacao*), Jojoba oil, petroleum jelly, dihydrogen oxide (H2O), Stearic acid (fatty acid), Anhydrous magnesium sulfate (Epsom salts) MgSO4 7H2O, glycerin, Zinc Oxide, and methods for using the composition to treat traumatic conditions of the skin including Stretch marks, wrinkles, age spots, facial or body scarring, Heat or thermal burns, radiation (sun) burns, rosacea, chapped (dry) lips and other traumatic skin conditions. And methods for mixing the composition.

BACKGROUND OF THE INVENTION

*Theobroma cacao* Extract Theobromine

Theobroma cocoa is now cultivated in Brazil, Costa Rica, Guayaquil, Ecuador, Venezuela, Peru, Guatemala, some West African countries, Ceylon, Samoa and other regions with similar Climates.

Reported to be an antiseptic, diuretic, ecbolic, emmenagogue, and parasiticide, cocoa is a folk remedy for alopecia, burns, cough, dry lips, fever, listlessness, malaria, nephrosis, parturition, rheumatism, snakebite, and wounds. Cocoa butter is even used to eliminate facial wrinkles.

The latest developments in cocoa/chocolate research, published in the Journal of the American Medical Association, include two clinical studies which indicate the flavanols found in Cocoa are beneficial to vascular health.

Chocolate contains chemicals similar to those found in Red Wine, Grape seed, and Green Tea that aids in blood circulation, reduces blood pressure, and provides other benefits. and body scarring, Heat or thermal burns and scarring, radiation (sun) burns, rosacea, chapped (dry) lips and other skin conditions Methods of Treatment The invention further provides methods of treating conditions of the skin of a human by topically treating the skin with the composition described in this invention. Exemplary ailments which may be treated using a topical composition of the present invention are radiation dermatitis, thermal burns, dermatomyofibromas, myositis, burns, diaper rash, itching, acne, sunburn, windburn, fever blister, cold sore, insect bite, insect sting, poison ivy, poison oak, poison sumac, dermatitis, other skin conditions, skin discoloration. Most specifically, the topical composition is used to treat Stretch marks, wrinkles, age spots, facial and body scarring, Heat or termal burns, radiation (sun) burns, rosacea, chapped (dry) lips and other skin conditions.

Specifically, treatment of Stretch marks, wrinkles, age spots, facial and body scarring, radiation (sun) burns and other skin conditions according to the invention is performed by topical application of the compositions of the invention to the affected area and is repeated from once to three times daily through out the course of treatment, specifically twice daily.

Specifically, treatment of radiation (sun) burns according to the invention is performed by topical application of the compositions of the invention to the affected area immediately after the burn is experienced and repeated from one to three times daily until the skin heals.

Specifically, treatment of age spots according to the invention is performed by topical application of the compositions to the affected areas and is repeated from one to two times daily until the skin heals, specifically two times daily after washing up the affected areas. Specifically in the morning and night until the age spots clears.

Recent studies confirm flavonoids, such as those in cocoa, decrease oxidation of LDL cholesterol, decrease the body's inflammatory immune responses, facilitate the dilation of arteries, and inhibit the aggregation of platelets in the bloodstream.

Theobromine
  MW: 180.17
  Formula: $C_7H_8N_4O_2$
Petroleum Jelly
White Petrolatum Petroleum jelly, petrolatum or soft paraffin is a semi-solid mixture of hydrocarbons (with carbon numbers mainly higher than 25), [2] originally promoted as a topical ointment for its healing properties. Its folkloric medicinal value as a "cure-all" has since been limited by better scientific understanding of appropriate and inappropriate uses. However, it is recognized by the U.S. Food and Drug Administration (FDA) as an approved over-the-counter (OTC) skin protectant and remains widely used in cosmetic skin care. The process of making petroleum jelly is under U.S. Pat. No. 127,568 filed in 1872.

Shea Butter

Shea butter or Shea nut butter is a slightly yellowish or ivory-colored natural fat extracted from fruit of the shea tree by crushing and boiling. Shea butter is widely used in cosmetics as a moisturizer and an emollient. Shea butter is also edible. It is used as a cooking oil in West Africa, as well as sometimes being used in the chocolate industry as a substitute for cocoa butter.

The shea or karite tree, formerly *Butyrospermum paradoxum*, is now called *Vitellaria paradoxa*. It produces its first fruit (which resemble large plums) when it is about 20 years old and reaches its full production when the tree is about 45 years old. It produces nuts for up to 200 years after reaching maturity.

Many vernacular names are used for *Vitellaria*, which is a reflection of its extensive range of occurrence—nearly 5,000 km from Senegal (west) to Uganda (east) across the African continent. The nomenclature history and synonymy of the shea tree followed a very tortuous evolution since the oldest recorded specimen collected by a European—Scottish explorer Mungo Park—dated May 26, 1797. It eventually arrived at the name *vitellaria* with subspecies paradoxa and *nilotica*. It usually grows to an average height of about 15 m with profuse branches and a thick waxy and deeply fissured bark that makes it fire resistant.

The shea tree grows naturally in the wild in the dry savannah belt of West Africa from Senegal in the west to Sudan in the east, and onto the foothills of the Ethiopian highlands. It occurs in 19 countries across the African continent, namely Benin, Burkina Faso, Cameroon, Central African Republic, Chad, Ethiopia, Ghana, Guinea Bissau, Cote d'Ivoire, Mali, Niger, Nigeria, Senegal, Sierra Leone, Sudan, Togo, Uganda, Zaire and Guinea.

Properties

Shea butter is known especially for its cosmetic properties as a moisturizer and emollient. It is also a known anti-inflammatory agent.[1] Shea butter is marketed as being effective at treating the following conditions: fading scars, eczema, burns, rashes, acne, severely dry skin, blemishes, dark spots, skin discolorations, chapped lips, stretchmarks, wrinkles, and in lessening the irritation of psoriasis. Shea butter provides natural ultraviolet sun protection, although the level of protection is extremely variable, ranging from nothing to approximately SPF 6. Shea butter absorbs rapidly into the skin without leaving a greasy feeling. In Nigeria, it is known to be very effective in the management of sinusitis and relief of nasal congestion.[2] This is due to its emollient properties which helps in relaxing the tension in the face skin thus easing respiration. All one needs do, if one has sinus problems or congestion, is rub a considerable amount of the butter in and around the nostrils.

Jojoba Oil

Jojoba (pronounced ho-ho-ba) oil is a vegetable oil obtained from the crushed bean of the jojoba shrub (*Simmondsia chinenis*). The jojoba shrub is native to the Sonoran Desert of northwestern Mexico and neighboring regions in Arizona and southern California. It grows in dense stands throughout that region. The woody evergreen shrub may reach 15 ft (4.5 m) in height. Jojoba has flat gray-green leathery leaves and a deep root system that make it well adapted to desert heat and drought. It has a life span of 100-200 years, depending on environmental conditions. Jojoba grows best in areas with 10-18 in (25-45 cm) of annual rainfall where temperatures seldom fall below 25° F. (−4° C.) for more than a few hours at night. It can grow on many types of soils including porous rocks, in slightly acid to alkaline soils, and on mountain slopes or in valleys.

Jojoba shrubs are dioecious, meaning plants are either male (staminate), producing pollen, or female (pistillate), producing flowers. The small flowers have no odor or petals and do not attract pollinating insects. The flowers are pollinated by wind in late March; the flowers develop into fruit by August, with full maturation occurring by October. The green fruit dries in the desert heat, its outer skin shriveling and pulling back to expose a wrinkled brown soft-skinned seed (referred to as a nut or bean) the size of a small olive. These nuts, which resemble coffee beans, contain a vegetable oil that is clear and odorless but less oily to the touch than traditional edible oils. The oil comprises half of the weight of the nut. There are about 1,700 seeds in a pound; 17 lb (6.3 kg) of jojoba seeds are required to produce one gallon of oil.

Native Americans have used jojoba for hundreds of years. In the 1700s, Father Junipero Serra, the founder of 21 California missions, noted in his diary that the Native Americans were using the oil and the seeds for many different purposes: for treating sores, cuts, bruises, and burns; as a diet supplement and as an appetite suppressant when food was not available; as a skin conditioner, for soothing windburn and sunburn; as a cooking oil; as a hair or scalp treatment and hair restorative; and as a coffee-like beverage by roasting the seeds.

The chemical structure of jojoba oil is different from that of other vegetable oils. Rather than being an oil, it is actually a polyunsaturated liquid wax that is similar to sperm whale oil, though without the fishy odor. It is made of fatty acids as well as ester composed entirely of straight chain alcohols. Both the acid and alcohol portions of jojoba oil have 20 or 22 carbon atoms, and each has one unsaturated bond. Waxes of this type are difficult to synthesize. As a wax, jojoba oil is especially useful for applications that require moisture control, protection, and emolliency. Jojoba oil is liquid at room temperature because of its unsaturated fatty acids. It does not oxidize or become rancid and does not break down under high temperatures and pressures. Jojoba oil can be heated to 370° F. (188° C.) for 96 hours without exhibiting degradation in general composition and carbon chain length. The stability shown by jojoba oil makes it especially useful for cosmetic applications.

When the United States banned the use of sperm whale oil (spermaceti wax) in 1974, the government began to fund efforts to investigate and cultivate jojoba as a replacement. Jojoba oil was found to be an adequate substitute for applications that had previously used sperm whale oil. The first commercial cultivation of jojoba was in the Negev Desert and Dead Sea areas of Israel, but by 1977, domestic cultivation had begun in the United States General Use Jojoba oil has many uses in a wide variety of industries. As a cosmetic, it is an effective cleanser, conditioner, moisturizer, and softener for the skin and hair. It is applied directly to the skin to soften the skin, to reduce wrinkles and stretch marks, to lighten and help heal scars, and to promote healthy scalp and hair. Jojoba oil is similar to, and miscible with, sebum, which is secreted by human sebaceous glands to lubricate and protect skin and hair. When sebum production decreases due to age, pollutants, or environmental stresses, jojoba oil can be used to replicate sebum oil. Jojoba oil can accumulate around hair roots, thereby conditioning hair and preventing it from becoming brittle and dull. If there is too much sebum buildup on the scalp, it dissolves and removes the sebum, leaving the hair clean. Jojoba oil as a solubilizing agent can also remove sticky buildup on hair from hair preparations as well as airborne particulates deposited on the hair. It forms a lipid layer on the skin, acting as a moisturizer, as well as penetrating and being absorbed by the outer layer of skin. It is widely used as an ingredient in shampoos, conditioners, facial, hand and body lotions, cuticle and nail care products, baby care lotions, creams, and oils, cleansers, moisturizers, bath oils and soaps, sunscreen lotions, and makeup products. Jojoba oil is also used as a base in the manufacture of perfume. The potential therapeutic uses of jojoba oil include the treatment of acne, cold sores, and such skin diseases as psoriasis.

Jojoba oil is also a registered (licensed for sale) pesticide for use on crops. It is used to control white flies on all crops and powdery mildew on grapes and ornamentals. It is applied as a spray containing 1% or less final concentration of jojoba oil. It acts as a pesticide by forming a physical barrier between an insect pest and the leaf surface. Because of its low toxicity and its rapid degradation in the environment, jojoba oil does not pose a risk to non-target organisms or the environment; though as an oil, it should not be disposed of in lakes or other bodies of water.

Zinc Oxide Use and Formulation

Zinc oxide is a natural source pigmented mineral, quarry mined and further refined to a fluffy white powder. It is commonly found in cosmetics as a whitening agent and it is also found in sunscreens because of its impressive capability to block UV light. Zinc Oxide has an enormous refractive index (ability to bend light) and comes in right under the refractive capabilities of diamonds. This is why it is the first choice for powerful sunscreens.

Zinc oxide lozenges are a popular over-the-counter cold remedy, but numerous studies have failed to demonstrate any significant effect. Zinc oxide in a mixture with about 0.5% iron(III) oxide ($Fe_2O_3$) is called calamine and is used in calamine lotion. There are also two minerals, zincite and hemimorphite, which have been called calamine historically (see: calamine (mineral)). When mixed with eugenol, the mixture is called zinc oxide eugenol and has restorative and prosthodontic applications in dentistry. Zinc peroxide, $ZnO_2.1/2\ H_2O$, is a white to yellow powder that is used in antiseptic ointments.

Zinc oxide is added to many breakfast cereals, as a source of zinc; a necessary nutrient. (Other cereals may contain zinc sulfate, for the same purpose.) Some prepackaged foods also include trace amounts.

Production Methods

Zinc oxide is produced by two main processes:

French Process

Metallic zinc is melted in a graphite crucible and vaporized above 907° C. Zinc vapor instantaneously reacts with the oxygen in the air to give ZnO, accompanied by a drop in its temperature and bright luminescence. Zinc oxide particles are transported into a cooling duct and collected in a bag house. This indirect method is commonly known as the French process (FP) which was popularised by LeClaire (France) in 1844. A typical FP, zinc oxide normally consists of agglomerated zinc oxide particles with an average size of 0.1 micrometers to a few micrometers. By weight, most of the world's zinc oxide is manufactured via French process and major applications involve industries related to rubber, varistors, sunscreens, paints, healthcare, and poultry nutrients. Recent developments involve acicular nanostructures (rods, wires, tripods, tetrapods, plates) synthesized using a modified French process known as catalyst-free combust-oxidized mesh (CFCOM) process. Acicular nanostructures usually have micrometer-length nanorods with nanometric diameters (below 100 nm).

The so-called direct method is related to the FP. In this process, zinc ores or roasted sulfide concentrates are mixed with coal. In a reduction furnace, ore is reduced to metallic zinc and the vaporized zinc is allowed to react with oxygen to form zinc oxide.

American Process

In this process ore of zinc (zinc ash) is dissolved (as $ZnCl_2$) and precipitated with alkali. Zinc oxide made from this process is known as "Active Zinc Oxide".

Safety

As a food additive, Zinc oxide is generally recognized as safe by the FDA.

Zinc oxide itself is non-toxic, however it is hazardous to breathe zinc oxide fumes. Fumes of zinc oxide are generated when zinc or zinc alloys are melted and oxidized at high temperature. This occurs while melting brass, because the melting point of brass is close to the boiling point of zinc. Exposure to zinc oxide in the air, which also occurs while welding galvanized (zinc plated) steel, can result in a nervous malady called metal fume fever. For this reason, typically galvanized steel is not welded, or the zinc is removed first.

Magnesium Sulfate

Magnesium sulfate is a chemical compound containing magnesium and sulfate, with the formula $MgSO_4$. In its hydrated form the pH is 6.0 (5.5 to 7.0). It is often encountered as the heptahydrate, $MgSO_4.7H_2O$, commonly called Epsom salt. Anhydrous magnesium sulfate is used as a drying agent. Since the anhydrous form is hygroscopic (readily absorbs water from the air) and therefore harder to weigh accurately, the hydrate is often preferred when preparing solutions, for example in medical preparations. Epsom salt has been traditionally used as a component of bath salts.

Occurrence

Magnesium sulfates are common minerals in geological environments. Their occurrence is mostly connected with supergene processes. Some of them are also important constituents of evaporitic potassium-magnesium (K—Mg) salts deposits. Almost all known mineralogical forms of $MgSO_4$ occur as hydrates. Epsomite is the natural analogue of "Epsom salt,"

Applications

Magnesium sulfate is used in bath salts, particularly in flotation therapy where high concentrations raise the bath water's specific gravity, effectively making the body more buoyant. This property is also used to restore some Lava lamps damaged by being shaken by exchanging the water and adding drops of a concentrated solution until sustainable buoyancy is reached. Traditionally, it is also used to prepare foot baths, intended to soothe sore feet. The reason for the inclusion of the salt is partially cosmetic: the increase in ionic strength prevents some of the temporary skin wrinkling ("pruning"—partial maceration) which is caused by prolonged immersion of extremities in pure water. However, magnesium sulfate can also be absorbed into the skin, reducing inflammation. It is also sometimes found in bottled mineral water, and accordingly is sometimes listed in the contents thereof. It may also be used as a coagulant for making tofu.

Magnesium sulfate heptahydrate is also used to maintain the magnesium concentration in marine aquaria which contain large amounts of stony corals as it is slowly depleted in their calcification process. In a magnesium-deficient marine aquarium calcium and alkalinity concentrations are very difficult to control because not enough magnesium is present to stabilize these ions in the saltwater and prevent their spontaneous precipitation into calcium carbonate.

Medical Use

Oral magnesium sulfate, or magnesium hydroxide, is commonly used as a saline laxative. Epsom salt is also available in a gel form for topical application in treating aches and pains.

Indications for its Use are

Solutions of sulfate salts such as Epsom salt may be given as first aid for Barium chloride poisoning.

Magnesium sulfate paste has been used as an agent for dehydrating (drawing) boils, carbuncles and abscesses.

Magnesium sulfate solution has also been shown to be an effective aid in the fight against blemishes and acne when applied directly to problematic areas, usually in poultice form. Magnesium sulfate when used through soaking, can soothe muscle pains and help improve rough patches in the skin.

The body's magnesium level increases when soaking with magnesium sulfate which is necessary for serotonin, a mood-regulating neurotransmitter that may increase feelings of relaxation and well-being.

Soaking in a warm bath containing Epsom Salt (magnesium sulfate) can be beneficial to soothe and relieve Herpes outbreak symptoms, such as itching and lesions relating to Genital Herpes and Shingles.

Stretch Marks

Stretch marks or striae, as they are called in dermatology, are a form of scarring on the skin with a silvery-white hue. They are caused by tearing of the dermis, and over time can diminish but not disappear completely. Stretch marks are the result of the rapid stretching of the skin associated with rapid growth (common in puberty) or weight gain (e.g. pregnancy) that overcomes the dermis's elasticity. Although stretch marks are generally associated with pregnancy and obesity, they can also develop during rapid muscle growth. Medical terminology for these kinds of markings includes striae atrophicae, vergetures, stria distensae, striae cutis distensae, striae gravidarum (in cases where it is caused by pregnancy), lineae atrophicae, striae distensae, linea albicante, or simply striae. Symptoms and signs They first appear as reddish or purple lines, but tend to gradually fade to a lighter color. The affected areas appear empty and soft to the touch.

Stretch marks occur in the dermis, the resilient middle layer that helps the skin retain its shape. No stretch marks will form as long as there is support within the dermis. Stretching plays more of a role in where the marks occur and in what direction they run. Stretching alone is not the cause.

Stretch marks can appear anywhere on the body, but are most likely to appear in places where larger amounts of fat are stored. Most common places are the abdomen (especially near the belly-button), breasts, upper arms, underarms, thighs (both inner and outer), hips, and buttocks. They pose no health risk in and of themselves, and do not compromise the body's ability to function normally and repair itself.
Causes The glucocorticoid hormones responsible for the development of stretch marks affect the epidermis by preventing the fibroblasts from forming collagen and elastin fibers, necessary to keep rapidly growing skin taut. This creates a lack of supportive material, as the skin is stretched and leads to dermal and epidermal tearing. If the epidermis and the dermis has been penetrated, laser will not remove the stretch marks.
Prevention and Cure Between 75% and 90% of women develop stretch marks to some degree during pregnancy. The sustained hormonal levels as a result of pregnancy usually means stretch marks may appear during the sixth or seventh month.

Though cocoa butter is an effective moisturizer, no research studies have shown its ability to either prevent stretchmarks, or to reduce their appearance once a stretchmark has already formed.

Various treatments are available for the purpose of improving the appearance of existing stretch marks, including laser treatments, dermabrasion, and prescription retinoids. Some cream manufacturers claim the best results are achieved on recent stretch marks; however, few studies exist to support these claims.

A study in the journal *Dermatologic Surgery* showed that radiofrequency combined with 585-nm pulsed dye laser treatment gave "good and very good" subjective improvement in stretch marks in 33 of 37 patients, although further studies would be required to follow up on these results. In addition, the use of a pulsed dye laser was shown to increase pigmentation in darker skinned individuals with repeated treatments.

A surgical procedure for removing lower abdominal stretch marks is the tummy tuck, which removes the skin below the navel where stretch marks frequently occur.

A new modality, fractional laser resurfacing, offers a novel approach to treating striae. Using scattered pulses of light only a fraction of the scar is zapped by the laser over the course of several treatments. This creates microscopic wounds and as such is a "no downtime" procedure. The body responds to each treatment by producing new collagen and epithelium. In a 2007 clinical trial, 5-6 treatments resulted in striae improving by as much as 75%.

Wrinkles

You can often get an idea of how old someone is by looking at his or her face—specifically the skin. As people age, it's normal to get wrinkles. If the person has spent a lot of time in the sun, at tanning salons, or smoking cigarettes, he or she might have a lot of them.

The skin is made up of three layers: the outermost layer everyone can see, called the epidermis (say: eh-puh-dur-mis) the middle layer, called the dermis (say: dur-mis) the innermost layer, called the subcutaneous (say: sub-kyoo-tay-nee-us) layer. When a person is young, he or she doesn't have wrinkles because the skin does a great job of stretching and holding in moisture. The dermis has an elastic quality thanks to fibers called elastin that keep the skin looking and feeling young. A protein in the dermis called collagen (say: ka-luh-jun) also plays a part in preventing wrinkles.

However, over time, the dermis loses both collagen and elastin, so skin gets thinner and has trouble getting enough moisture to the epidermis. The fat in the subcutaneous layer that gives skin a plump appearance also begins to disappear, the epidermis starts to sag, and wrinkles form.

There's not a magic age (like 40) when everyone suddenly gets wrinkles. Some people in their 20s have little wrinkles around their eyes (called "crow's feet") from squinting or spending too much time in the sun.

Other people may be in their 50s or 60s before you can even see a wrinkle. This is usually because they have taken good care of their skin over the years and may have more sebum (say: see-bum), the skin's natural oil. They may also have "good genes"—which means their family members don't have many wrinkles. Eventually, however, everyone will have at least a few wrinkles. It's a natural part of the aging process.
Scars Scars (also called cicatrices) are areas of fibrous tissue that replace normal skin (or other tissue) after injury. A scar results from the biologic process of wound repair in the skin and other tissues of the body. Thus, scarring is a natural part of the healing process. With the exception of very minor lesions, every wound (e.g. after accident, disease, or surgery) results in some degree of scarring.

Scar tissue is not identical to the tissue that it replaces and is usually of inferior functional quality. For example, scars in the skin are less resistant to ultraviolet radiation, and sweat glands and hair follicles do not grow back within scar tissue. A myocardial infarction, commonly known as a heart attack, causes scar formation in the heart muscle, which leads to loss of muscular power and possibly heart failure. However, there are some tissues (e.g. bone) that can heal without any structural or functional deterioration.

The word scar was derived from the Greek word eschara, meaning place of fire (fireplace)
How Scarring Occurs A scar is a natural part of the healing process. Skin scars occur when the deep, thick layer of skin (the dermis) is damaged. The worse the damage is, the worse the scar will be. Most skin scars are flat, pale and leave a trace of the original injury that caused them. The redness that often follows an injury to the skin is not a scar, and is generally not permanent. The time it takes for it to go away may, however, range from a few days to, in some serious and rare cases, a few years. Various treatments can speed up the process in serious cases.

Scars form differently based on the location of the injury on the body and the age of the person who was injured. To mend the damage, the body has to lay down new collagen fibres (a naturally occurring protein that is produced by the body). Recent research has implicated the gene osteopontin in scarring. The University of Bristol has developed a gel that inhibits the process. This process results in a fortuna scar. Because the body cannot re-build the tissue exactly as it was, the new scar tissue will have a different texture and quality than the surrounding normal tissue. An injury does not become a scar until the wound has completely healed.

Transforming Growth Factors (TGF) play a critical role in scar development and current research is investigating the manipulation of these TGFs for drug development to prevent scarring from the emergency adult wound healing process. As well, a recent American study implicated the protein Ribosomal s6 kinase (RSK) in the formation of scar tissue and found that the introduction of a chemical to counteract RSK could halt the formation of Cirrhosis. This treatment also has the potential to reduce or even prevent altogether other types of scarring.

Liver Spot

Liver spots are blemishes on the skin associated with aging and exposure to ultraviolet radiation from the sun. They are also known as age spots, sun spots, lentigos, or senile/solar lentigines. They range in color from light brown to red or black and are located in areas most often exposed to the sun, particularly the hands, face, shoulders, arms and forehead, and the head if bald. Liver spots are not related to the liver physiologically, but do have a similar color. It was once believed, incorrectly, that liver spots were due to liver problems.

From the age of 40 onwards the skin is less able to regenerate from sun exposure, and liver spots are very common in this age group, particularly in those who spend time in the sunshine.

In the vast majority of cases liver spots pose no threat, and no treatment is necessary. Occasionally, they have been known to obscure the detection of skin cancer.

Some people wish to have these spots removed as they consider them unsightly

Sunburn

A sunburn is a burn to living tissue such as skin produced by overexposure to ultraviolet (UV) radiation, commonly from the sun's rays. Usual mild symptoms in humans and animals are red or reddish skin that is hot to the touch, general fatigue, and mild dizziness. An excess of UV-radiation can be life-threatening in extreme cases. Exposure of the skin to lesser amounts of UV radiation will often produce a suntan.

Cause

The cause of sunburn is the direct damage that a UV-B photon can induce in DNA. One of the possible reactions from the excited state is the formation of a thymine-thymine cyclobutane dimer. This kind of damage is responsible for only 8% of all melanoma. Sunburn is caused by the UV-radiation stemming from the sun, from tanning lamps, or from welding arcs. It is a reaction of the body to the direct DNA damage which can result from the excitation of DNA by UV-B light. This damage is mainly the formation of a thymine-thymine dimer. The damage is recognized by the body, and it triggers several defense mechanisms. These include DNA repair to revert the damage and increased melanin production to prevent future damage. Melanin transforms UV-photons quickly into harmless amounts of heat without generating free radicals and is therefore an excellent photoprotectant against direct and indirect DNA damage. Sunburn is one of the potential dangers of ultraviolet germicidal irradiation.

On an evolutionary level, the sunburn may have developed as a warning signal that deters humans from sun seeking behaviour which induces infertility. Importantly it has been shown that protecting against sunburn with chemical sunscreens does not imply protection against other damaging effects of UV-radiation.

Heat or Thermal Burns

Heat or thermal burns occur when the skin touches a hot surface. The skin may either be in contact with hot liquids, flames, steam, flash, or extremely hot surfaces. The minimum temperature that could cause heat burns is 115° F. This can occur anywhere at home like exposure to irons, stoves, hot kettles, and others.

Although 75% of the reported burns can be inhibited, it is still necessary to know the degree of your burn. Classification of the burn depends on what stage or layer of the skin is affected. The severity of your burns determines what kind, for how long and to what extent of treatment is going to be rendered.

Causes of Burns

The most common sources of thermal burns are heat and fire. Scalds or extremely hot steams are also known to be the cause of thermal burns in households especially for children and housewives.

Medical Attention

If you're suffering from too much pain, it is advisable that you seek your doctor's advice for necessary treatment. If sensitive areas like eyes, joints, hands, feet, ears, genitals, or joints are affected, request for emergency medical attention. It is recommended that you see a doctor in these following situations:

The thickness of the burn grows more than twice its original size

When the thickness appears to be charred, dry and numb

Majority of your body is swelling due to the burn

If you have difficulty in breathing

If unconsciousness results from the thermal burn

Treatment

Certain medications are available for burn treatments. One example is a topical antibiotic which can contain triple major ingredients namely Silvadene, Neosporin, and Bacitracin. Pain relievers are also sufficient to alleviate the pain born from the burn. Some of the common over-the-counter pain relievers are acetaminophen and ibuprofen. If severe pain still persists, doctors may recommend Tylenol as an anesthetic pain reliever. Medical experts have their own common procedures on attending heat or thermal burns. The burned area is cleansed before removing damaged or dead tissues. But blisters that may have developed on the hands and feet may be left untouched to avoid further pain.

First-Aid Care

It is essential to know the basic steps to home care in case you receive thermal burns.

1. Put out the fire—If your clothes are in flame, take them off or you can drop and roll to put out the fire. Avoid the risk of being in contact with hot steam or surfaces.

2. Cold Treatment—Be sure to immediately cool the burned area with tap water for a few minutes. This can minimize the extent of the burn.

3. Antibiotic Ointments—These are effective for mild burns. Not only do they heal wounds but they also prevent further infection.

4. Blisters—Do not attempt to remove blisters on your own. Be sure that you seek your doctor's advice on procedures regarding blisters on your feet and hands.

SUMMARY OF THE INVENTION

The need exists for a topical treatment of skin conditions including stretch marks, wrinkles, age spots, facial and body scarring, radiation (sun) burns, rosacea, chapped (dry) lips and other skin conditions. This Inventor has discovered that direct topical application of the right proportions of shea butter, jojoba oil and a suitable amount of a pharmaceutically acceptable carrier, and optionally, one or more of the following: Magnesium Sulphate (MgSo4.7H2O) and Zinc Oxide (ZnO) can help the skin to start healing itself. The advantages of this invention are its remarkable success in the treatment of conditions of the skin; Stretch marks, wrinkles, age spots, facial and body scarring, Heat or termal burns, radiation (sun) burns, rosacea, chapped (dry) lips and the ease of preparation. The compositions require no elaborate and protracted separation procedures but are prepared by mixing the components, immediately after which the compositions may be applied topically to the affected skin.

DETAILED DESCRIPTION OF THE INVENTION

Definitions

Jojoba oil has many uses in a wide variety of industries. As a cosmetic, it is an effective cleanser, conditioner, moisturizer, and softener for the skin. It is applied directly to the skin to soften the skin, to reduce wrinkles and stretch marks, to lighten and help heal scars, and to promote healthy scalp and hair. Jojoba oil is similar to, and miscible with, sebum, which is secreted by human sebaceous glands to lubricate and protect skin and hair. When sebum production decreases due to age, pollutants, or environmental stresses, jojoba oil can be used to replicate sebum oil. Jojoba Oil is sold by retailers such as Jedwards International, Inc. Quincy Mass.

Magnesium sulfate solution has been shown to be an effective aid in the fight against blemishes and acne when applied directly to problematic areas, usually in poultice form. Magnesium sulfate can be absorbed into the skin, reducing inflammation. Magnesium Sulphate is sold by retailers such as Concepts Ringwood Ill. and or Alcan Specialty Chemicals in Stamford, Conn. (United States) or Thinker Chemical Company, Ltd., of Hangzhou 310018, China.

Shea butter is known especially for its cosmetic properties as a moisturizer and emollient. It is also a known anti-inflammatory agent.

Shea butter is marketed as being effective at treating the following conditions: fading scars, eczema, burns, rashes, acne, severely dry skin, blemishes, dark spots, skin discolorations, chapped lips, stretchmarks, wrinkles, and in lessening the irritation of psoriasis. Shea butter provides natural ultraviolet sun protection, although the level of protection is extremely variable, ranging from nothing to approximately SPF 6. Shea butter absorbs rapidly into the skin without leaving a greasy feeling. Shea butter is sold by retailers such as JedwardsInternational, Inc. Quincy Mass. and or Oils By Nature Solon, Ohio.

Zinc oxide is a natural source pigmented mineral, quarry mined and further refined to a fluffy white powder. It is commonly found in cosmetics as a whitening agent and it is also found within sunscreens because of its impressive capability to block UV light. Zinc oxide is sold by retailers such as Alcan Specialty Chemicals in Stamford, Conn., US (United States)

Pharmaceutically acceptable carriers are selected from those well known to those of ordinary skill in the art including, but not limited to, those listed in reference texts such as REMINGTON'S PHARMACEUTICAL SCIENCES 17th Edition, Mack Publishing Company 1985, they are also readily available from wholesalers well known to those of ordinary skill in the art.

According to the invention, the pharmaceutically acceptable carrier may be selected from the group consisting of cocoa butter, petroleum jelly, jojoba oil, olive oil, soybean oil, coconut oil, petrolatum, petroleum jelly, beeswax, lanolin wax, carnauba wax, stearic acid and mixtures thereof.

In a specific embodiment of the invention, the pharmaceutically acceptable carrier is cocoa butter.

Compositions

The present invention relates to compositions for the treatment of stretch marks, wrinkles, age spots, blemishes, facial and body scarring, radiation (sun) burns, rosacea, chapped (dry) lips and other skin conditions, comprising of shea butter, jojoba oil and optionally, one or more of the following: Magnesium Sulphate (MgSo4), Zinc Oxide (ZnO) and a suitable amount of a pharmaceutically acceptable carrier. The compositions diminished and cleared these traumatic skin conditions with remarkable success.

The specific proportions of the invention that have produced success in treating these conditions of the skin are: (a) Anhydrous magnesium sulfate (Epsom salts) MgSO4 7H2O in an amount ranging from about 0.002% to about 6% by, Shea butter in an amount ranging from about 0.2% to about 35%, Jojoba oil in an amount ranging from about 0.02% to about 20%, petroleum in an amount ranging from about 0.02% to about 19%, Glycerin in an amount ranging from about 0.02% to about 5%, Stearic acid (fatty acid) in an amount ranging from about 0.002% to about 10%, Zinc Oxide in an amount ranging from about 0.002% to about 5% by weight; mixed with dihydrogen Oxide (H2O) in an amount ranging from about 0.002% to about 50% by volume and about 0.02% to 60% of a pharmaceutically acceptable carrier, The total weight of the composition is up to about 200,000 mg, specifically, between about 90,000 mg and about 100,000 mg, and most specifically, about 110,000 mg, in about 50 g of pharmaceutically acceptable carrier.

The preferred embodiment of the invention, magnesium sulfate (Epsom salts) MgSO4 7H2O is present in an amount between about 500 mg and about 6000 mg, and shea butter is present in an amount between 26,000 mg to about 32,000 mg, and most jojoba oil is present in an amount between 15,000 mg to about 21,500 mg, Zinc oxide is present in an amount between 800 mg to about 1,200 mg; petroleum jelly is present in an amount between 11.00 mg to about 14,000 mg; Stearic acid is present in an amount between 3,800 mg to about 6,000 mg, glycerin is present in an amount between 850 mg to about 1,500 mg; dihydrogen oxide (H2O) is present in an amount between 13,500 ml to about 16,000 ml in about 25 g to about 33 g of the pharmaceutically acceptable carrier.

The pharmaceutically acceptable carrier is cocoa butter.

The basic composition is prepared by weighing and measuring the ingredients to be used, combining them, and mixing them gently until, the desired consistency is obtained.

Also provided are topical compositions as described herein characterized in that it is active against conditions of the skin, specifically stretch marks, wrinkles, age spots, facial Specifically, treatment of rosacea according to the invention is performed by topical application of the compositions to the affected areas and is repeated from one to two times daily until the skin heals, specifically two times daily after washing up the affected areas. Specifically in the morning and night until the affected area clears.

Specifically, treatment of dry or chapped lips according to the invention is performed by topical application of the compositions to the affected areas and is repeated from one to two times daily until the skin heals, specifically two times daily. Specifically in the morning and night until the lips heal.

Specifically, prevention and treatment of wrinkles according to the invention is performed by topical application of the compositions of the invention to the skin two or three times daily. Specifically in the morning and night.

Specifically, treatment of facial and body scars according to the invention is performed by topical application of the compositions of the invention to the scarred areas of the skin two or three times daily. Specifically in the morning and night.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

Example 1

The present example relates to a specific embodiment of the composition of the invention. The specific ingredients are magnesium sulfate (Epsom salts) MgSO4.7H2O, shea butter, jojoba oil, Zinc oxide, petroleum jelly, Stearic acid, glycerin, dihydrogen oxide (H2O) and cocoa butter. The ingredients are weighed and measured, combined, and gently mixed until a desired consistency is obtained.

Example 2

The following table relates to the general variations and proportions of the composition within the scope of the invention:

TABLE 1

| Ingredients | Variable % | Variable % | Variable % |
| --- | --- | --- | --- |
| Cacao Butter | 29 | 25 | 30 |
| Water H2O | 15 | 13 | 18 |
| Shea Butter | 35 | 32 | 29 |
| Jojoba Oil | 13 | 16 | 10 |
| Petroleum Jelly | 11 | 12 | 14 |
| Glycerin | 1 | 1.5 | 1 |
| Stearic Acid | 9 | 5 | 6 |
| Magnesium Sulphate (MgSo4.7H2O) | 2 | 2.5 | 3 |
| Zinc Oxide | 1.9 | 1 | 1 |

Example 3

The following table relates to the variations and proportions of the composition within the scope of the invention with mineral foundation:

TABLE 1

| Ingredients | Variable % | Variable % | Variable % |
| --- | --- | --- | --- |
| Cacao Butter | 29 | 25 | 30 |
| Water H2O | 15 | 13 | 18 |
| Shea Butter | 35 | 32 | 29 |
| Jojoba Oil | 13 | 16 | 10 |
| Petroleum Jelly | 11 | 12 | 14 |
| Glycerin | 1 | 1.5 | 1 |
| Stearic Acid | 9 | 5 | 6 |
| Magnesium Sulphate (MgSo4.7H2O) | 2 | 2.5 | 3 |
| Zinc Oxide | 1.9 | 1 | 1 |
| Mineral Foundation | 1 | 1 | 1.5 |

Example 4

The present example relates to the method of treatment of reducing the appearance of wrinkles by topical application of the composition of the invention, as specifically described in EXAMPLE 1. A 38 year old female was starting to show signs of aging around the mouth, eyes and forehead. Because her facial skin was sensitive to most products over the counter, the subject used the cream on half of her face twice a day, morning and night. By the fifth day, the areas treated with the cream had shown remarkable improvement. After five days she started treating her whole face and after 31 days of using the composition, her facial skin showed no signs of aging. This result was attributed to the cream.

Example 5

A female subject used the cream to treat scars (black spots) caused by zits/pimples on her face twice a day, morning and night. By the third day, her face showed remarkable improvement. After 14 days (two weeks) of using the composition, her facial skin showed no signs scarring from zits/pimples. This result was attributed to the cream. She began using the invention as her facial cream to prevent any more facial scarring. At the same time her face had a more youthful appearance with no signs of aging.

Example 6

The present example relates to the method of reducing age sports by application of the composition of the invention, specifically as described in EXAMPLE 1. A female subject in her early sixties. When she was young she had frequently exposed her skin to a lot of sun. She had age sports and weathered skin on her arms, chest area and face. To prevent further damage she applied the composition of the invention on her affected areas twice a day; In the morning and at night. After eight weeks her age spots were less prominent than before.

Example 7

This example relates to the method of treating body scars by the application of the composition of the invention. The subject had scars from teenage years caused by falling, scraping her knees and other accidents. Now in her late thirties she started using the cream. A noticeable improvement was observed within one month of applying the cream. After two months the scared tissue continued to improve by softening and blending with the rest of the skin.

Example 8

This example relates to the method of treating heat or thermal scars by the application of the composition of the invention. The subject burned her hand on the stove. She started applying the composition on the red scar two times a day. The wound healed without leaving a significant scar.

I claim:

1. A composition effective for diminishing, healing and clearing conditions of the skin; stretch marks, blemishes, wrinkles, age spots, facial and body scarring, heat or thermal burns or scarring, radiation burns, dry skin, rosacea, and chapped lips, the composition comprising:
   (a) $MgSO_4 \cdot 7H_2O$ (Epsom salts) in an amount from 2% to 10% by weight,
   (b) shea butter in an amount from 29% to 51% by weight,
   (c) jojoba oil in an amount from 10% to 25% by weight,
   (d) petroleum jelly in an amount from 11% to 18% by weight;
   (e) glycerin in an amount from 1% to 30% by weight,
   (f) stearic acid in an amount from 5% to 30% by weight,
   (g) zinc oxide in an amount from 1% to 10% by weight,
   (h) water in an amount from 0.002% to 60% by weight, and about 0.02% to 60% of a pharmaceutically acceptable carrier.

2. The composition according to claim 1 further comprising:
   (i) cocoa butter in an amount from 0.02% to 55% by weight.

3. The composition according to claim 2 further comprising mica in an amount from 0.002% to 10% by weight, titanium dioxide in an amount from 0.002% to 10% by weight, iron oxides in an amount from 0.002% to 10% by weight, and ultramarine blue in an amount from 0.002% to 10% by weight.

4. The composition according to claim 3 wherein the total combined amount of mica, titanium dioxide, iron oxides, and ultramarine blue is from 0.002% to 20% by weight.

5. The composition according to claim 1 wherein the jojoba oil is present in a volume of 2 ml to 21 ml.

6. The composition according to claim 1 wherein the shea butter is present in an amount of 2 g to 35 g.

7. A composition effective for soothing traumatic conditions of the skin, stretch marks, wrinkles, age spots, facial and body scarring, heat or thermal burns or scarring, radiation burns, dry skin, rosacea, and chapped lips, the composition comprising:
   (a) $MgSO_4 \cdot 7H_2O$ (Epsom salts) in an amount from 2% to 5% by weight,
   (b) shea butter in an amount from 29% to 32% by weight,
   (c) jojoba oil in an amount from 10% to 19% by weight,
   (d) petroleum jelly in an amount from 11% to 15% by weight;
   (e) glycerin in an amount from 1% to 3% by weight,
   (f) stearic acid in an amount from 5% to 7% by weight,
   (g) zinc oxide in an amount from 1% to 3% by weight,
   (h) water in an amount from 0.002% to 17% by weight, and about 0.02% to 60% of a pharmaceutically acceptable carrier.

8. The composition according to claim 7 wherein the water is present in a volume of 10 ml to 60 ml.

9. The composition according to claim 7 wherein the $MgSO_4 \cdot 7H_2O$ (Epsom salts) is present in an amount of 0.03 g to 4 g by weight.

10. The composition according to either claim 1 or claim 7 wherein the composition is formulated as a lotion, foundation cream, cream, lip balm, lipstick, or a topical composition suitable to be applied to the skin or hair.

* * * * *